United States Patent [19]

Wissler

[11] 4,343,793

[45] Aug. 10, 1982

[54] PROCESS FOR OBTAINING INTACT AND VIABLE LEUCOCYTES AND THROMBOCYTES FROM BLOOD

[75] Inventor: Josef H. Wissler, Bad Nauheim, Fed. Rep. of Germany

[73] Assignee: Max-Planck Gesellschaft zur Forderung der Wissenschaften, Gottingen, Fed. Rep. of Germany

[21] Appl. No.: 237,703

[22] Filed: Feb. 24, 1981

[30] Foreign Application Priority Data

Mar. 10, 1980 [DE] Fed. Rep. of Germany ....... 3009126

[51] Int. Cl.³ ........................ A61K 35/14; A01N 1/02
[52] U.S. Cl. ......................................... 424/101; 435/2
[58] Field of Search .............................. 424/101; 435/2

[56] References Cited

U.S. PATENT DOCUMENTS 3,709,791  1/1973  Lichtenstein ........................... 435/2

OTHER PUBLICATIONS

Tullis—Blood, vol. 7, (1952), pp. 891–896.
Böyum, A., *Nature*, 204: 793–794 (1964).
Day, R. P., *Immunology*, 18: 955–959 (1970).
Feige, U., et al., *Immunobiology*, 157: 217 (1980).
Graubner, M., et al., *Inn. Med.* 4: 316–324 (I) and 380–387 (II) (1977).
Johnson, T. M., und Garvin, J. E., *Proc. Soc. Exp. Biol. Med.*, 102: 333–335 (1959).
Kretschmer, V., und Meuller-Eckhardt, Ch. *Blut*, 35: 415–418 (1977), especially the abstract.
Kretschmer, V., und Mueller-Eckhardt, Ch. *Infusionstherapie*, 5: 298–320 (1978), especially the abstract.
Kuramochi, T., *Journal of Immunological Methods*, 5: 65–69 (1974).

Loos, J. A., and Roos, D., *Exp. Cell Res.*, 86: 333–341 (1974).
Nobel, P. P., and Cutts, J. H., *J. Lab. Clin. Med.*, 72: 533–538 (1968).
Shortman, K., et al., *J. Cell Biol.*, 48: 566–579 (1971).
Strelkauskas, A. J., et al., *J. Immunol.*, 120: 1278–1282 (1978).
Thierfelder, S., *Vox Sang.*, 9: 447–454 (1964).
Ting, A. & Morris, P. J., *Vox Sang*, 20: 561–563 (1971).
Thorsby, E. & Bratlie, A., Histocompatibility Testing 1970 (ed. P. I. Terasaki), pp. 655–656, Munksgaard, Copenhagen 1970.
v. Heyden, H. W., *Proc. Soc. Exp. Biol. Med.*, 139: 1181–1184 (1972).
Nyegaard & Co. AS, Oslo Sodium Metrizoate Solution for Isolation of Blood Cells., A/S Stjerne-Trykk, Nr. 746-75.
Pharmacia Fine Chemicals AB, Uppsala: Ficoll for cell research. Sven Hallberg Reklam/Upplands Grafiska AB, Mar. 1973–1976.
Pharmacia Fine Chemicals AB, Uppsala: Dextran Fractions, dextran sulfate, DEAE-dextran. Defined polymers for biological research. Upplands Grafiska AB, Dec. 1974–1975.

*Primary Examiner*—Sam Rosen
*Attorney, Agent, or Firm*—Kenyon & Kenyon

[57] ABSTRACT

A process for obtaining functionally and morphologically intact and viable leucocytes and thrombocytes from blood is disclosed. Erythrocytes are removed from the blood and then the leucocytes are separated by centrifugation and treated to remove trace amounts of erythrocytes and thrombocytes. The thrombocytes are obtained from the supernatant produced by the centrifugation.

11 Claims, No Drawings

PROCESS FOR OBTAINING INTACT AND VIABLE LEUCOCYTES AND THROMBOCYTES FROM BLOOD

BACKGROUND OF THE INVENTION

The present invention relates to a method of separating blood components. More specifically, it relates to a method of obtaining functionally and morphologically intact leucocytes and thrombocytes.

Leucocytes (white blood cells) are trace cell components of the blood. They perform various functions in the body, such as the defense against infections, the degradation of destroyed biological material (phagocytosis), and the production of materials regulating cell growth and natural resistance such as hormones, immunological mediators and immunoglobulins, prostaglandins, and histamine. Undesirable or impaired functions of the leucocytes are manifest in allergy, tumor survival and in leukaemias in the form of unimpeded cell division of certain leucocyte types and of their precursors. Leucocytes behave like amoeboid cells and can be stimulated to migrate at random (chemokinesis) as well as directionally under the influence of a concentration gradient (chemotaxis) of distinct chemical agents (chemoattractants) in their environment. These two kinds of migration behavior are among the most sensitive criteria in studying the functional viability and intrinsic vital capacity of leucocytes.

There are various types of leucocytes: neutrophil, eosinophil and basophil phagocytes, mononuclear phagocytes (monocytes), and small mononuclear leucocytes (lymphocytes), as well as numerous different types of precursors. The lymphocytes in turn consist of different distinguishable subpopulations with various biological functions (T cells, B cells and the like). All types of leucocytes are formed in the bone marrow as multipotent parent cells capable of proliferation and differentiation. These parent cells are also the precursors of erythrocytes and thrombocytes. After maturation and passage into the blood stream, only the monocytes and lymphocytes retain their capacity to divide. The passage of the various kinds of leucocytes from the blood stream into the tissue as a result of chemoattraction in general is again associated with a further differentiation of the cells. For example, monocytes are converted into macrophages and basophil leucocytes into mast cells. Leucocytes are very sensitive cells, with a limited cell type-depending lifespan. The influence of external forces and the effect of numerous kinds of chemical substances or non-physiological conditions provoke both their functional and morphological damage.

So far, only small quantities of leucocytes (maximum of about $10^{10}$ cells per batch) can be obtained economically by existing preparation processes. For this purpose, for example, the entire leucocyte population is separated directly from the whole blood with the aid of so-called separating agents for two-phase systems by centrifugation or by gravitational forces [A. Boyum, *Scand. J. Lab. Invest.*, 21, Suppl. 97 (1968)]. Similar processes are known to obtain only certain types of leucocytes, e.g. only neutrophil granulocytes of lymphocytes, by joint separation of all the other components of the blood. These known processes of direct separation are not suitable for obtaining larger quantities of leucocytes. [M. Graubner, et al, *Inn. Med.*, 4, 316 and 380 (1977)]. They require large volumes of expensive separating agents for two-phase systems. Thus, a sample of 100 liters of blood would require about 150 liters of a "leucocyte two-phase-separation-fluid", for example, metrizoate-ficoll, density 1.077 g/ml, according to known procedures. [Nyegaard & Co., *A/S Stjerne-Trykk*, Nr. 746-75] The handling or in particular the centrifugation of very large volumes of whole blood or even larger volumes of dilutions of whole blood with such a separating agent remains an unsolved technical problem. The application of continuous flow-through centrifugation has been proposed as a solution to this problem. Attempts have also been made for magnetic separation of certain types of leucocytes, such as neutrophil granulocytes, which previously have phagocytosed additions of small magnetic iron particles. Techniques for separation of leucocytes from blood by aid of adsorption at specially prepared surfaces and filters (leucapheresis) are also in use. A further variant is the isolation of the so-called "buffy coat" in which leucocytes are partially aggregated or dead, by sedimentation at $1 \times g$ of all cellular blood constituents. For various reasons all these processes only allow preparation of leucocytes from smaller quantities of blood (maximum about 6 to 10 liters).

In addition to the mentioned difficulties in handling, extremely high costs of known processes for leucocyte separation result from the use of the necessarily large amounts of very expensive two-phase system separation and cell aggregation agents (metrizoate, dextran, and the like) [A. Boyum, *Scand. J. Clin. Lab. Invest.*, 21, Suppl. 97 (1968)] and the specially prepared surfaces for differential leucocyte adsorption. In particular they deliver leucocytes whose functional and morphological integrity and viability are questionable. This applies above all to the continuous flow-through centrifugation method, in which the forces acting upon the leucocytes are highly irregular, and applies also to the isolation techniques by magnetic forces.

"Functional integrity" means substantially unimpaired random and directional locomotion capacity, unimpaired phagocytosis of foreign particles and cell-specific secretion of leucocyte products. "Morphological integrity" is commonly determined by the integrity of the cell shape and of the sub-cellular structures as well as by the negative adsorption of dyes of higher molecular weight by living cells in the dye exclusion test (vital staining).

A prerequisite for research of the biological functions of leucocytes, for the preparation of leucocyte hormones on a large scale, and for the medico-diagnostic and medico-technical applications of leucocytes is the availability of large quantities of functionally and morphologically intact and viable leucocytes. For example, in order to obtain about 1–10 mg of distinct leucocyte hormones, e.g., growth controlling factors, interferon, and the like, which are biologically active at nanomolar concentrations and are secreted by a molecularly homogeneous leucocyte culture, it is estimated that 50 kg of leucocytes must be available. This corresponds to processing about 10,000 liters of blood. Therefore, rapid, cell-sparing, effective and economical techniques are necessary to obtain pure leucocytes on a technical scale. The same considerations apply accordingly to thrombocytes.

It is, therefore, a primary object of this invention to provide a process for obtaining leucocytes from large amounts of blood.

It is another object of this invention to provide a process for obtaining leucocytes from blood in functionally and morphologically intact state.

It is another object of this invention to provide a process for obtaining high yields of large amounts of functionally and morphologically intact and viable leucocytes from blood.

It is still another object of this invention to provide a process which allows effective, economical, rapid and cellsparing preparation of a high yield of large amounts of leucocytes.

It is still another object of this invention to provide a process for obtaining from blood large amounts of thrombocytes which are functionally and morphologically intact and in a viable state.

These and other objects and advantages of the present invention will be evident from the following description of the invention.

SUMMARY OF THE INVENTION

The invention accordingly involves a process for obtaining functionally and morphologically intact and viable leucocytes from blood and comprises the following steps.

(a) The blood is contacted with a sufficient quantity of an erythrocyte-aggregating substance to produce a liquid component and aggregated erythrocytes.

(b) The liquid component from step a is centrifuged at a maximum speed corresponding to an average force of about $400 \times g$ and at a temperature of about 0° to 37° C. for about 5 to 15 min to produce a thrombocyte-containing supernatant and sedimented leucocytes.

(c) The sedimented leucocytes from step b are treated to lyse the remaining accompanying erythrocytes and thrombocytes by the addition of water or a sodium chloride solution of up to 0.4 wt% sodium chloride. The pH of the water or salt solution is about 6.0 to 8.5 and the maximum temperature allowed is about +8° C. The treatment is conducted for about 20 to 60 sec., after which the suspension is readjusted to the physiological concentration and the leucocytes are separated from the suspension.

Homogeneous subpopulations of cells may be obtained from these preparations by standard techniques.

DETAILED DESCRIPTION OF THE INVENTION

Through the process in accordance with the invention, therefore, the entire viable leucocyte population, including all the various leucocyte types, is isolated in a free-floating, non-aggregated form which does not contain erythrocytes, thrombocytes, plasma, or serum components.

It is also not necessary to add large amounts of two-phase separating agents to the blood in order to achieve a separation of certain types of cells from large volumes of blood. The fact that no two-phase separating agents are used for the separation of the bulk volume of whole blood makes the process not only more economical and faster, but also does not stress the sensitive cells. It thus allows isolation of the leucocytes in a high yield and better maintains their functional and morphological integrity.

After the separation of the whole mixed populations of leucocytes, individual types of leucocytes can then be separated by using conventional separating agents for two-phase systems and techniques. However, for this latter purpose, smaller and thus more economical quantities of special and expensive chemicals may be used since the volume to be treated has been reduced to a small fraction (about 0.5%) of the original volume of blood. Furthermore, if two-phase separating agents are used to obtain distinct pure leucocyte populations after the process of the invention has been used to eliminate major plasma constituents, no leucocyte-activating mediators are created by the interaction of two-phase separation agents with plasma protein systems.

The process of the invention is suitable for obtaining the leucocytes from blood of all kinds of organisms. Because of its easy availability, the use of mammalian blood, especially human, porcine, bovine, sheep, canine, rabbit, guinea-pig, or rat blood is preferred. The blood can be used in the native anticoagulated state or coagulated as a cell-rich serum. Native anticoagulated blood is preferred, since the separation of cell-rich serum from the blood clot makes necessary an additional operation and involves an essential loss of thrombocytes as well as partial loss of phagocytes as a result of adhesion to and inclusion in the blood clot. To prevent coagulation, normal anticoagulants such as citrates, oxalates, EDTA, or heparin can be added to the native blood in the usual quantities. For reasons of economy a citrate solution is the preferred anticoagulant.

In the first step of the process the blood is contacted with a sufficient quantity of an erythrocyte-aggregating substance [A. Boyum, *Scan. J. Clin. Lab. Invest.*, 21, Suppl. 97 (1968); S. Reklam, *Upplands Grafiska AB*, March 1973–6; *Upplands Grafiska AB*, Sec. 1974–5] to separate the bulk of erythrocytes (about 50% of the blood volume) from the whole free-floating, non-aggregated leucocyte populations and the thrombocytes. This separation is accomplished without the use of separating agents for two-phase systems and/or centrifugation. All substances normally used for this purpose, which do not damage or aggregate leucocytes, are suitable as erythrocyte-aggregating materials. Special examples of such substances are methylcellulose, dextran, and other natural and synthetic polysaccharides.

Methylcellulose is preferably used as the erythrocyte-aggregating substance. It is a cheap and the most economical agent. It is also physiologically unobjectionable. Furthermore, it does not activate the complement and other blood protein systems when used at the required low concentrations and other conditions. Therefore, no humoral leucocyte-activating factors are released by the preparation process. Methylcellulose of the lowest possible viscosity is used to facilitate the handling of the suspension and separation of the erythrocytes. Methylcellulose with a viscosity of greater than $10^{-2}$, and preferably $2 \times 10^{-2}$ to $3 \times 10^{-2}$ Pa.s, is suitable. The viscosity is measured on a 2% solution in water at 20° C.

Such preferred methylcellulose has an average molecular weight of about 20,000 to 25,000. The minimum concentration of the methylcellulose added to the blood is about 0.01%. At lower concentrations the aggregating action is unsatisfactory, the precipitation of the erythrocytes takes too long, and the leucocytes are also deposited partially in aggregated form, as the so-called buffy coat. The upper limit of the methylcellulose concentration is not critical. It is determined by the aspects of viscosity and economy. Based on these factors, concentrations above about 0.3% are not expedient. A concentration range of about 0.05 to 0.3% is preferred. The most preferred concentration is about 0.1% methylcellulose in the whole blood suspension.

The treatment with the erythrocyte-aggregating substance such as methylcellulose is done at temperatures of 0° to 37° C. and and a pH of about 5.0 to 9.0, preferably 6.8 to 7.5.

After the addition of the methylcellulose the erythrocyte aggregates are deposited within a period of about 20 to 35 minutes. The liquid component which consists of plasma, leucocytes, thrombocytes, and small amounts of residual erythrocytes, is then removed from the aggregated erythrocytes using typical known procedures such as decantation, skimming, or pumping off. A volume reduction of about 50% is achieved in this way.

The second step of the process of the invention involves the joint separation of all leucocyte populations from the thrombocytes and plasma constituents in the leucocyte- and thrombocyte-rich liquid component of the first step. For this purpose, the liquid component is briefly centrifuged at low speed. All the types of leucocytes are sedimented together while the plasma constituents and the thrombocytes remain in the supernatant.

The centrifugation must not be performed at higher than a maximum speed corresponding to average force about 400×g. Higher speeds sediment thrombocytes as well. The lower limit of the centrifugation speed is not critical; however, if it is too low, longer centrifuging will be necessary which can lead to losses in yield and may result in impaired functional integrity of the leucocytes. The centrifugation is preferably performed at an average force of about 400×g.

The duration of the centrifugation is 5 to 15 minutes. If a shorter period is used, the sedimentation effect is incomplete. If longer times are used, the functional integrity of the leucocytes is impaired. The centrifugation is preferably performed for about 8 to 12 minutes, and in particular for about 10 minutes. The temperature during the centrifugation can range from 0° to 37° C. It preferably may be 0° to about 15° C., most preferably 5° to 10° C.

Any manual or automatic centrifuge capable of being maintained at a constant speed and temperature is suitable for this purpose.

At the end of the centrifugation, the supernatant rich in thrombocytes and plasma constituent is separated from the sedimented leucocytes using typical procedures such as decantation, skimming, or pumping off. The volume of the leucocyte sediment is now about 0.5% of the initial volume of blood.

In accordance with the invention, the thrombocytes can be separated as a sediment from the plasma constituents from the thrombocyte-rich supernatant by brief centrifugation in the manner described above, but at forces higher than 400×g, preferably at 800×g, over a period of 20 minutes. Then, they can be suspended in a salt solution that does not damage or aggregate thrombocytes and are thus ready for any further use. An optional procedure is to wash at least once the thrombocyte sediment in order to free it from adherent plasma constituents. In this procedure cells are dispersed in a liquid and at conditions that do not damage or aggregate thrombocytes. Thereafter, the thrombocytes are recollected as sediment by centrifugation in the above manner at 800×g within a period of 20 minutes. The isolation of thrombocytes in this way is likewise an object of the process in accordance with the invention.

The plasma-containing supernatant can be used separately or in association with the thrombocytes.

The leucocyte sediment obtained by the step described above contains a small quantity of residual accompanying erythrocytes and thrombocytes. These cellular contaminants are lysed and then removed in the third step of the process in accordance with the invention, by suspension of the cells in a hypotonic solution of common salt or in water.

For this purpose, the leucocyte sediment is dispersed by careful slow circular shaking with water or a dilute solution of sodium chloride adjusted to a maximum NaCl concentration of 0.4% at a pH of about 6.0 to 8.5 and a maximum temperature of about +8° C. over a period of about 20 to 60 sec. Under these conditions the erythrocytes and thrombocytes are destroyed by lysis and their components are released into the solution, while the leucocytes remain functionally and morphologically intact. A concentration of sodium chloride higher than about 0.4% and/or an exposure period shorter than about 20 sec. are inadequate for complete lysis of the foreign cells. A treatment period longer than 60 sec. and/or a temperature above +8° C. also damage the various types of leucocytes.

The pH during the lysis is preferably kept at about 6.8 to 7.5, and in particular at about 7.1. The maximum temperature should preferably be about 4° C. and in particular about 0° to 1° C. The preferred duration of the lysis is about 25 to 35 sec. and in particular about 30 sec. In addition, a maximum NaCl concentration during lysis of about 0.2% is preferred. An optimal volume of the suspension to be adjusted for the lysis reaction is about 1/20 of the original volume of blood.

The lysis reaction is stopped by the reconstitution of physiological saline conditions, preferably 0.9% sodium chloride. For example, in the case of a cell suspension with an NaCl content of 0.2%, this is achieved by addition of the same volume of 1.6% sodium chloride solution at the same temperature and the same pH with careful slow circular swirling. The final volume obtained is one tenth of the original blood volume or about a 20-fold volume over the volume of the leucocyte sediment. Hence, the cellular products released by the lysis step and small amounts of residual plasma constituents are concomitantly washed out of the remaining intact leucocytes. The functionally and morphologically intact leucocytes are then separated from the suspension. This can be done, for example, by centrifugation under the conditions of the second step of the procedure (preferably at average forces of about 400×g for about 8 to 12 min at a maximum temperature of about 15° C.). Thereafter, the supernatant is removed from the sedimented leucocytes, for example by decantation, skimming or pumping off.

In a preferred form of the process of the invention, the leucocyte sediment obtained in the third step is at least once suspended by dispersion of the cells by slow circular swirling in a liquid medium that does not damage or aggregate leucocytes. Then, the leucocytes are separated again from this liquid medium to remove small quantities of soluble contaminants adherent to the cells. A suitable liquid medium for this purpose is any liquid that does not damage or aggregate the cells, preferably physiological saline or protein solutions (cell culture media) or cryopreservative media. Special examples of suitable solution are physiological saline, Hank's, Gey's, or Earle's balanced saline solutions. Other known, non-harmful cell media are also acceptable. For an effective washing process, the volume of the suspension is adjusted to about 1/10 of the original volume of whole blood. Hence, this corresponds to a 20-fold volume compared to the leucocyte suspension. The result is at least a 400-fold dilution of the original lysis debris contaminants and about a 80,000-fold dilution of total blood plasma contaminants. The washed solution can then be separated by known procedures from the sediment after a centrifuging step, by, for example, decantation, skimming, or pumping off.

In another method the leucocytes suspended in the washing liquid can be used as such or in the form of a sediment. They can also be cryopreserved in accordance with techniques known to those skilled in the art.

All the steps of the process in accordance with the invention are preformed under sterile conditions if this is required for the use in consideration and for maintenance of the functional and morphological integrity of the leucocytes over their normal lifespan. The vessels used must have hydrophobic (e.g. siliconized or teflon-coated) surfaces to prevent loss of various leucocyte types and thrombocytes by adhesion and thus, cause changes in the natural composition of the population. As a result of the limited natural lifespan of leucocytes, the process for obtaining them must be performed in as short a time as possible. As essential advantage of the process of the invention consists in the fact that it makes it possible to prepare the leucocytes without interruption in a time which is relatively short as compared to their lifespan.

In the process in accordance with the invention, functionally and morphologically intact and viable leucocytes can be obtained in a large quantity and in an economical manner. For example, about $5 \times 10^{12}$ cells can be isolated in one batch per operator. The leucocytes obtained can be used for various purposes as a whole population. For example, the mixed population can be cultured and used for the production of leucocyte hormones for tissue repair and other biologically active molecules of natural resistance. It can also be used for the isolation of the cell components or sub-cellular structures intrinsic of vital leucocytes.

It is also possible to isolate individual types of leucocytes in homogeneous cell populations from the mixed populations of leucocyte types by using common techniques in use for whole blood. However, since the volume to be processed is now considerably smaller than the original volume of whole blood, the separation and isolation of individual types of leucocytes on a larger scale with the use of the known, usual separating agents for two-phase systems and use other methods known to those skilled in the art is possible and can be performed on an economical basis. For example, a suspension of the leucocytes maintained in three volumes of liquid requires only about 2% of that amount necessary for the original blood volume. This constitutes a further advantage of the process in accordance with the invention.

For example, the granulocytes, i.e., the neutrophil, eosinophil and basophil leucocytes, can be separated from the mononuclear leucocytes, i.e., lymphocytes and monocytes, by treating the entire populations with glass wool. In this process, the granulocytes and macrophages adhere to the glass wool but the mononuclear lymphocytes do not and, therefore, can be selectively washed out. By selective elution with an appropriate liquid medium that detaches but does not damage or aggregate the leucocytes, the functionally and morphologically intact granulocytes can thereafter be obtained from the glass wool. Both the granulocytes and the mononuclear lymphocytes can then be cultured separately or can otherwise be used.

The invention is further illustrated by the following example. The example, however, does not constitute a limitation of the invention which is fully described above.

EXAMPLE (a) 100 liters of fresh sterile porcine blood is converted into anticoagulated blood by the addition of heparin to a concentration of 10 U/ml or sodium citrate to a final concentration of 0.01 M, the pH being 7.10. This blood is placed in a sterile, siliconized, cylindrical, 120-liter container made of polypropylene. The blood is then overlayed or mixed with a 2% aqueous solution of methylcellulose (MC 25; average molecule weight 25,000) to a concentration of 0.1 (W/V)%. This overlay or mixture is allowed to stand ($1 \times g$) for 35 min at 10° C. Then, the liquid component (about 50% of total blood volume), which contains leucocytes and thrombocytes, is separated from the aggregated erythrocytes.

(b) The liquid component obtained is immediately centrifuged for 10 min at 5° C. and $400 \times g$. The thrombocyte-containing supernatant is decanted from the sedimented leucocytes and immediately centrifuged for 20 min at $800 \times g$. By these means the thrombocytes are separated as sediment from plasma protein constituents. In addition, a washing step for removal of residual plasma protein constituents can be performed by gently suspending the sedimented thrombocytes in the buffered physiological saline mentioned above or any other cell culture medium which additionally contains 0.01 mol/liter sodium citrate to prevent aggregation of thrombocytes. Thereafter, the cells can be recollected by centrifugation as mentioned.

(c) The sedimented leucocytes are then carefully dispersed by circular shaking for 30 sec at 0° C. in a 1 m mol/liter sodium-potassium phosphate buffer solution at pH 7.10, containing sodium chloride at a concentration of 0.2 (W/V)% which lyses the remaining accompanying erythrocytes and thrombocytes. The lysis process is stopped by the addition of an equal volume of a 1.6 (W/V)% solution of sodium chloride at pH 7.10 (in the same buffer), cooled to a temperature of 0° C. In this manner, the physiological concentration of 0.9 (W/V)% of sodium chloride is restored. The resulting dispersion of functionally intact and viable leucocytes is centrifuged for 10 min at 0° C. and $400 \times g$.

The mixed population of sedimented leucocytes obtained is sufficiently pure for many purposes, for example, cell-culturing processes, biological experiments, or further processing to pure leucocyte populations. For use as the starting material for special culture purposes, such as mediator production with the exclusion of contaminations of residual erythrocyte and thrombocyte components, the sedimented leucocytes are subjected to at least one further washing step.

(d) In this further washing step, the sedimented leucocytes are dispersed for about 10 min by careful slow circular swirling in the above mentioned 0.9 (W/V)% salt solution at 0° C. and pH 7.10 which used in an amount equal to 1/10 of the initial volume of blood (10 liters). The dispersion is then centrifuged for 10 min at 0° C. and $400 \times g$. This process is repeated a second time.

A mixed population of leucocytes is obtained in an average yield of 50%. In an application of these procedures to porcine blood, a total $2 \times 10^{12}$ cells represented by mixed leucocyte population can be isolated from 200 liters of the porcine blood which corresponds to about 1 kg of living cells.

Using standard methods known to those skilled in the art, the mixed leucocyte population obtained can either be cryopreserved or be separated into homogenous cell populations of neutrophil leucocytes (about 58% of the total mass of the leucocytes), lymphocytes (about 32%), monocytes (about 7%) eosinophils (about 2.5%), and basophils (about 0.5%).

What is claimed is:

1. A process for recovering leucocytes and thrombocytes from blood, which comprises:
   (a) contacting the blood with an erythrocyte-aggregating substance to produce a liquid component and aggregated erythrocytes and separating the aggregated erythrocytes from the liquid component;
   (b) centrifuging the liquid component at a speed having an average force of at most about $400 \times g$ and at a temperature of about 0° to 37° C. for about 5 to 15 min to produce a thrombocyte-containing supernatant and sedimented leucocytes and separating the sedimented leucocytes from the supernatant;
   (c) suspending the sedimented leucocytes in water or up to a 0.4% sodium chloride solution at a pH of about 6.0 to 8.5, and at a maximum temperature of about +8° C. for about 20 to 60 seconds, and thereafter readjusting the suspension to physiological concentration and separating the leucocytes from the suspension.

2. A process according to claim 1, which further comprises suspending the leucocytes from step c at least once in a liquid medium that does not damage or aggregate leucocytes and then separating the leucocytes from the liquid medium.

3. A process according to claim 1 wherein methylcellulose of low viscosity is used as the erythrocyte-aggregating substance.

4. A process according to claim 3 wherein methylcellulose with a viscosity of $(2-3) \times 10^{-2}$ Pa.s measured in a 2% solution in water at 20° C. is used.

5. A process according to claim 3 wherein the methylcellulose is used in a concentration of 0.05% to 0.3%.

6. A process according to claim 1 wherein the centrifugation of step b is carried out at an average force of $400 \times g$ and a maximum temperature of 15° C. for about 8 to 12 min.

7. A process according to claim 1 wherein step c is performed at a pH of about 6.8 to 7.5, a maximum temperature of 4° C., and an NaCl concentration of about 0.2% for about 25 to 35 sec.

8. A process according to claim 2 wherein a solution of physiological saline, preferably physiological sodium chloride, is used as the liquid medium that does not damage or aggregate leucocytes.

9. A process according to claim 1 which further comprises centrifuging the thrombocyte-containing supernatant of step b at a speed corresponding to an average force higher than $400 \times g$ over a period of 20 min to produce sedimented thrombocytes and a second supernatant containing the plasma constituents.

10. A process according to claim 9 which further comprises suspending the sedimented thrombocytes at least once in a liquid medium that does not damage or aggregate thrombocytes and then separating the thrombocytes from the liquid medium.

11. A process according to claim 1, which comprises:
   (a) contacting the blood with methylcellulose at about 0° to about 37° C. to produce a liquid component and aggregated erythrocytes and separating the aggregated erythrocytes from the liquid component, the methylcellulose having a viscosity of 2 to $3 \times 10^{-2}$ Pa.s as measured in a 2% solution in water at 20° C. and forming a concentration in the blood of 0.05% to 0.3%;
   (b) centrifuging the liquid component at a speed having an average force of $400 \times g$ and at a temperature of at most 15° C. for about 8 to 12 minutes to produce a thrombocyte-containing supernatant and sedimented leucocytes and separating the sedimented leucocytes from the supernatant;
   (c) suspending the sedimented leucocytes in a 0.2% sodium chloride aqueous solution at a pH of about 6.8 to 7.5 and at a temperature of at most 4° C. for about 25 to 35 seconds, and thereafter readjusting the suspension to physiological concentration and separating the leucocytes from the suspension;
   (d) centrifuging the thrombocyte-containing supernatant of step b at a speed corresponding to an average force of about $800 \times g$ over a period of 20 minutes to produce sedimented thrombocytes and a second supernatant and separating the sedimented thrombocytes from the second supernatant.

* * * * *